United States Patent
Halseth

(10) Patent No.: US 6,723,074 B1
(45) Date of Patent: Apr. 20, 2004

(54) SEQUENTIAL DELIVERY SYRINGE

(76) Inventor: Thor R. Halseth, 3737 Medea Creek Rd., Agoura Hills, CA (US) 91301

( * ) Notice: Subject to any disclaimer, the term of this patent is extended or adjusted under 35 U.S.C. 154(b) by 22 days.

(21) Appl. No.: 10/119,669

(22) Filed: Apr. 9, 2002

(51) Int. Cl.[7] ............................................. A61M 5/24
(52) U.S. Cl. ..................... 604/201; 604/81; 604/191; 604/203; 604/206
(58) Field of Search ..................... 604/200, 81, 191, 604/201, 203, 204, 206

(56) References Cited

U.S. PATENT DOCUMENTS

| | | | | |
|---|---|---|---|---|
| 3,911,916 A | * | 10/1975 | Stevens ........................ | 604/191 |
| 3,923,053 A | | 12/1975 | Weingarten | |
| 4,067,333 A | | 1/1978 | Reinhardt et al. | |
| 4,629,455 A | * | 12/1986 | Kanno ........................ | 604/241 |
| 4,702,737 A | * | 10/1987 | Pizzino ........................ | 604/191 |
| 4,747,829 A | * | 5/1988 | Jacob et al. .................. | 604/110 |
| 4,861,335 A | * | 8/1989 | Reynolds ..................... | 604/88 |
| 4,932,944 A | | 6/1990 | Jagger et al. | |
| 5,102,388 A | | 4/1992 | Richmond | |
| 5,308,322 A | * | 5/1994 | Tennican et al. ............... | 604/83 |
| 5,415,648 A | * | 5/1995 | Malay et al. ................. | 604/181 |
| 5,476,449 A | | 12/1995 | Richmond | |
| 5,509,912 A | * | 4/1996 | Vaillancourt et al. ......... | 604/537 |
| 5,637,087 A | * | 6/1997 | O'Neil et al. .................. | 604/82 |
| 5,709,668 A | * | 1/1998 | Wacks ......................... | 604/232 |
| 5,743,886 A | * | 4/1998 | Lynn et al. ................... | 604/191 |
| 5,776,113 A | * | 7/1998 | Daugherty et al. ........... | 604/537 |
| 5,950,986 A | * | 9/1999 | Daugherty et al. ...... | 251/149.6 |
| 6,485,471 B1 | * | 11/2002 | Zivitz et al. ................. | 604/212 |
| 6,524,278 B1 | * | 2/2003 | Campbell et al. ........... | 604/192 |
| 6,599,273 B1 | * | 7/2003 | Lopez ......................... | 604/249 |

* cited by examiner

*Primary Examiner*—Brian L. Casler
*Assistant Examiner*—Jeremy Thissell
(74) *Attorney, Agent, or Firm*—Jack C. Munro

(57) ABSTRACT

A sequential delivery syringe which has an internal chamber located within a body with the internal chamber being substantially closed at one end except for a discharge opening and totally open at the opposite end. A luer is connected to the discharge opening with the luer including a piercing member. A mid-piston is movably mounted within the internal chamber of the syringe with there also being a separate stopper piston which is connected to plunger. Between the stopper piston and the mid-piston is mounted a collapsible structure within which is an internal chamber. A liquid is to be contained within this internal chamber of the collapsible structure. Movement of the plunger and stopper piston toward the mid-piston will result in discharging any liquid contents which is located between the mid-piston and the closed end of the body, and upon the mid-piston being located directly adjacent the closed end, the mid-piston will be pierced which will permit the liquid that is contained within the collapsible structure to be discharged through the discharge passage following the discharge of the liquid which was contained within the syringe body and located between the mid-piston and the closed end.

5 Claims, 6 Drawing Sheets

SEQUENTIAL DELIVERY SYRINGE

BACKGROUND OF THE INVENTION

1. Field of the Invention

The subject matter of this invention relates to a syringe designed to contain two different liquid mediums and then permit the injection of the two different mediums sequentially into an IV line or a needle into a patient.

2. Description of the Related Art

Syringes are commonly used to inject medicine and saline solutions into a human or an animal. These injections usually occur by means of an IV (intervenous) line or needle which is connected into the body of the human or animal. Usually, the injected liquid that is contained within the syringe comprises a single liquid or a mixture of liquids. The syringe usually comprises a single internal compartment and has a single needle. Sometimes, the injection of medication requires the insertion of two different liquids. For example, there is a procedure that is known as a saline/heparin push. It is absolutely necessary that the saline be injected prior to the heparin because if the reverse occurs the IV line or needle will become immediately clogged requiring the IV line or needle to be removed and then reinstalled in position within the patient. Each removal and reinstallation is painful to the patient, time consuming to the doctor and nurse and costly to the medical facility not only in the extra time involved but because additional catheters, IV lines and syringes are required. Every year within the United States, there are literally billions of saline/heparin pushes administered. This means that every year there is a large number of mistakes that are made. At the current time, the heparin is contained within a syringe and the saline is contained within a separate syringe. Both syringes are essentially identical in size, quantity of liquid and color with the exception that one refers to heparin and the other refers to saline. It is relatively easy for the nurse to pick up the heparin syringe and administer that prior to administering of the saline.

The current practice includes an irrigation or cleansing flush consisting of a predetermined volume of saline (0.9 percent sodium chloride) delivered through a syringe. This is done to cleanse the inner lumen of the catheter of blood, medication or particulate matter. The saline flush is followed by an installation of heparin, via a syringe, to prevent occlusions (from blood or fibrin)n within the inner catheter lumen.

The Intravenous Nursing Society (INS) states that the volume of the flush should be equal to the priming volume of the catheter, plus any add-on pieces (i.e. extension sets) times two. This means that the volumes of the saline and heparin flushes could be identical. Medication errors frequently occur when the clinician or person delivering the flush confuses the two syringes and delivers the heparin flush first, followed by the saline flush. When this occurs, there is the increased potential of catheter occlusion if blood were to reflux into the distal catheter tip, since saline has no anticoagulant properties.

It would be desirable to utilize a single syringe which includes both the heparin and the saline where it is automatic that when making of the injection that the saline will be administered first and then the heparin will follow. In the past, there have been constructed multi-chamber syringes which are designed to accomplish this automatic sequential delivery of two different liquids. However, in the past, the sequential delivery syringes had to be prefilled and then be sterilized. The particular liquid in the syringe may be affected negatively by the sterilization procedure, which is usually radiation or heat. Therefore, at times it would be necessary to sterilize a sequential delivery syringe that contains only one of the liquids and then have some way to insert the second liquid into the syringe after the sterilization. It is believed that prior to the present invention there has not been known to utilize a novel sterile approach to the insertion of the second solution when constructing such a syringe.

Additionally, such a sequential delivery syringe could be used to deliver a medicament, such as an antibiotic followed by a quantity of saline. It would be desirable to construct a sequential delivery syringe that could be supplied to the physician or nurse that could be used to remove a precise quantity of medicament necessary for the particular patient and then administer that medicament and follow it with the saline solution.

SUMMARY OF THE INVENTION

The basic embodiment of the present invention comprises a sequential delivery syringe which has a body which includes an internal chamber. The body is substantially closed at one end but still provides access into an internal chamber through a through passage. The opposite end of the body is totally open. A luer is connected to the syringe at the one end with the luer including a discharge passage. The luer also includes a piercing member which extends within the internal chamber. A mid-piston is movably mounted within the internal chamber of the syringe with the mid-piston dividing the internal chamber into a front section and a rear section. A stopper piston, which is mounted on a plunger, is mounted in the rear section with this plunger extending exteriorly of the body of the piston. Also mounted within the rear section is a means for collapsing with the first liquid to be contained within this means. This means is normally closed. A second liquid is to be contained within the front section of the internal chamber. Upon movement of the plunger and the stopper piston toward the one end the second liquid is to be discharged through the discharge passage until the mid-piston is penetrated by the piercing member which provides access into the means for collapsing and permit the first liquid contained therein to be discharged through the discharge passage.

A further embodiment of the present invention is where the first basic embodiment is modified by the one end of the syringe body having a luer lock comprising a collar which surrounds an internal annular chamber and there is a tapered male luer centrally mounted within this annular chamber. It is the tapered female luer that is attached directly to the syringe.

A further embodiment of the present invention is where the previous embodiment is modified by the collar not having just a single opening through which to conduct the liquid into the discharge passage but there is actually a plurality of openings.

A further embodiment of the present invention is where the plurality of openings are located about the piercing member.

A further embodiment of the present invention is where the first basic embodiment is modified by the stopper piston including an air discharge valve.

A further embodiment of the present invention is where the first basic embodiment is modified by the means for collapsing comprising a flexible walled bag.

A further embodiment of the present invention is where the first basic embodiment is modified by the means for collapsing comprising a bellows.

A further embodiment of the present invention is where the first basic embodiment is modified by the piercing member being fixed to said body by being press fitted into a discharge passage formed within one end of the body.

A further embodiment of the present invention is where the first basic embodiment is modified by the piercing member being hollow having a circular sidewall with an opening formed in the sidewall spaced from the open end of outer end of the piercing member.

A further embodiment of the present invention is where the first basic embodiment is modified by the piercing member being hollow defined by a circular sidewall and an elongated slot is formed in the sidewall extending from the open outer end of the piercing member.

A further embodiment of the present invention is where the first basic embodiment is modified by the piercing member being mounted on a mounting disc with this mounting disc being placeable within the internal chamber of the body and being positioned directly adjacent the substantially closed one end of the body.

A further embodiment of the present invention is where the first basic embodiment is modified by the piercing member being mounted entirely through the mounting disc to be projected from both the front side and the back side of the mounting disc.

A second basic embodiment of the present invention comprises an integral one-piece syringe luer lock which is constructed to include a collar which has an internal chamber which is internally screw threaded. This collar is to facilitate, by the threads, attachment to an appropriate connector for discharge of the liquid into an IV line or needle which is connected to a patient. A male/female luer is mounted within the internal chamber with this male/female luer having a discharge passage, and it is through this passage that the injectable liquid is to be conducted. At least one opening is formed within the collar which connects to the internal chamber. A piercing member is mounted on the collar directly adjacent this opening. A female luer surrounds a portion of the piercing member with this female luer being mounted on the collar whereby a syringe liquid discharge tube is to be inserted within the female luer in a liquid-tight manner with the piercing member to then be located within the internal chamber of the syringe so as to penetrate a movable piston within the internal chamber of the syringe.

A further embodiment of the present invention is where the second basic embodiment is modified by the male/female luer being centrally mounted within the internal chamber.

A further embodiment of the present invention is where the second basic embodiment is modified by there being not just a single opening but a plurality of openings formed within the collar.

A further embodiment of the present invention is where the second basic embodiment is modified by the plurality of openings defined as being located about the piercing member.

A further embodiment of the present invention is where the second basic embodiment is modified by the piercing member being pressed fitted into said one end.

A further embodiment of the present invention is where the second basic embodiment is modified by the piercing member being hollow and having a circular sidewall, an opening formed within said sidewall spaced from the open outer end of the piercing member, said second liquid to be able to be conducted through said opening substantially emptying said internal chamber of said second liquid.

A further embodiment of the present invention is where the second basic embodiment is modified by the piercing member being hollow and having a circular sidewall, an elongated longitudinal slot formed in said sidewall extending from an open outer end of said piercing member.

A further embodiment of the present invention is where the second basic embodiment is modified by the piercing member being mounted on a mounting disc, said mounting disc being placeable within said internal chamber and being located directly adjacent said one end.

A further embodiment of the present invention is where the second basic embodiment is modified by the piercing member extending entirely through said mounting disc.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE INVENTION

Figure 1:
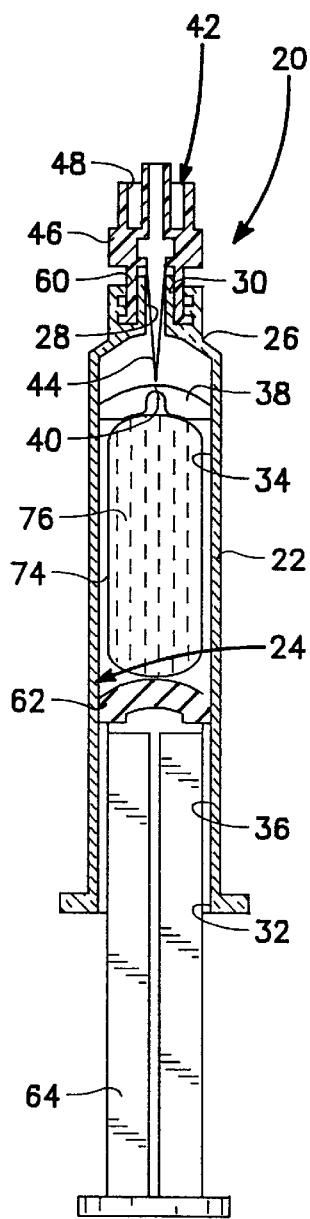
FIG. 1 is a longitudinal cross-sectional view of the sequential delivery syringe of the present invention showing the syringe as it would be supplied to a hospital, doctor's office or other medical facility.
Figure 2:
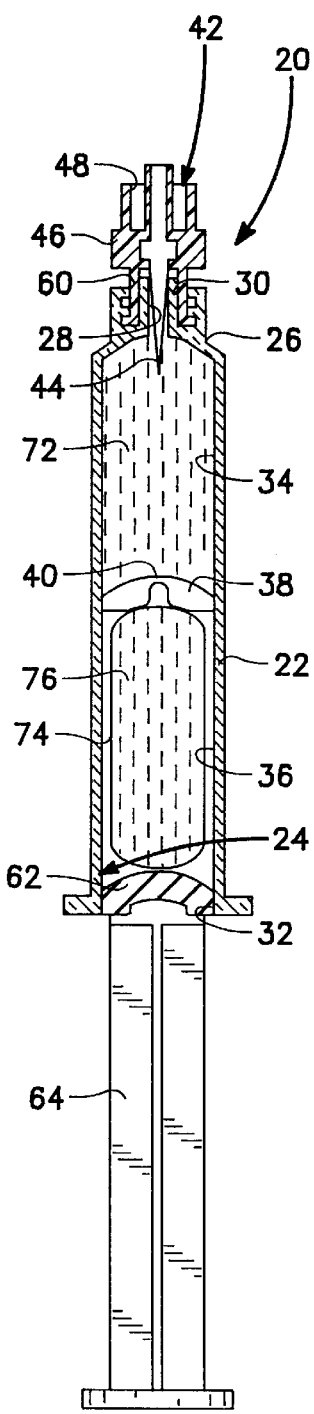
FIG. 2 is a view similar to FIG. 1 but showing the syringe in the position of adding a medicament or solution within the front compartment of the syringe by retracting of the plunger of the syringe.
Figure 3:
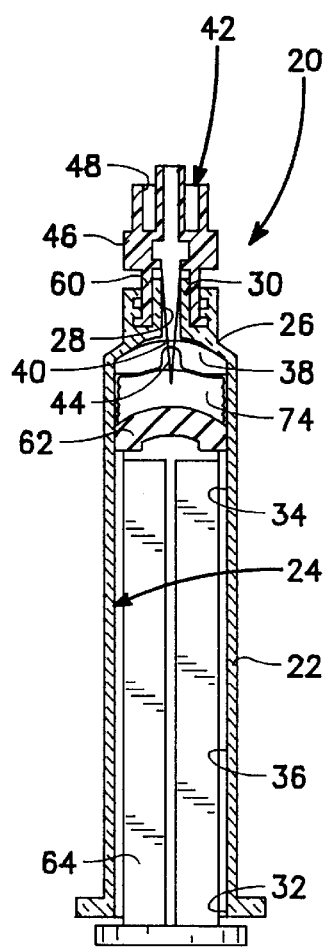
FIG. 3 is view similar to FIG. 2 but showing the syringe in the position of having completely injected both liquids that were contained within the body of the syringe.

Referring particularly to the drawings, there is shown in FIGS. 1–3 the first embodiment 20 of this invention. The first embodiment 20 shows a cylindrically shaped syringe body 22 which has an internal cylindrical chamber 24. Although the internal chamber 24 is shown to be cylindrical as well as the body 22 being cylindrical, it is considered to be within the scope of this invention that the body 22 could be other than cylindrical and also the chamber 24 could be other than cylindrical. For example, the body 22 and chamber 24 could be square, rectangular, hexagonal, octagonal or even triangular in shape. Also, the body 22 and the cylindrical chamber 24 could be oval.

The body 22 has a substantially closed end 26. Formed within the closed end 26 is an outlet passage 28. Outlet passage 28 is formed within a slightly tapered syringe liquid discharge tube 30. The rear end of the body 22 is entirely open forming an access opening 32.

For purposes of the description, the internal cylindrical chamber 24 will be described as having a front section 34 and a rear section 36. Referring particularly to FIG. 2 of the drawings, there is mounted a mid-piston 38 within the internal chamber 24 that provides a separating wall between the front section 34 and the rear section 36. This mid-piston 38 includes a rubber or plastic narrowed section 40 which is capable of being pierced by a sharp instrument.

A male/female luer lock 42 is to be mounted in conjunction with the closed end 26. There are available conventional luers that could be utilized in conjunction with the body 22 of this invention. However, the conventional luers utilize a metallic needle as a piercing device which must be mounted separately in conjunction with the plastic structure that makes up the body of the luer 42. It would be desirable to construct a luer lock where the piercing device, in the form of a spike 44, is made of plastic and integral with a cylindrically shaped collar 46. The collar 46 has an annular internal chamber 48 which surrounds a tapered male luer 50. Formed within the tapered male luer 50 is a discharge passage 52. The annular internal chamber 48 includes a series of screw threads 54. These screw threads 54 are to be adapted to tightly connect with a connector, which is not shown, which is to be connected to an IV line, which is also not shown, or an IV needle, which is not shown.

Formed within the collar 46 surrounding the spike 44 are a series of holes 56. There will actually be four in number of the holes 56 surrounding the spike 44. However, the number of the holes could be increased or decreased without departing from the scope of this invention. For example, a single hole will probably be more than satisfactory. The holes 56 connect internal chamber 58 with the discharge passage 52. The internal chamber 58 is formed within a female luer 60. The female luer 60 surrounds a portion of the spike 44 with the tip area of the spike 44 extending exteriorly of the female luer 60.

Figure 9:
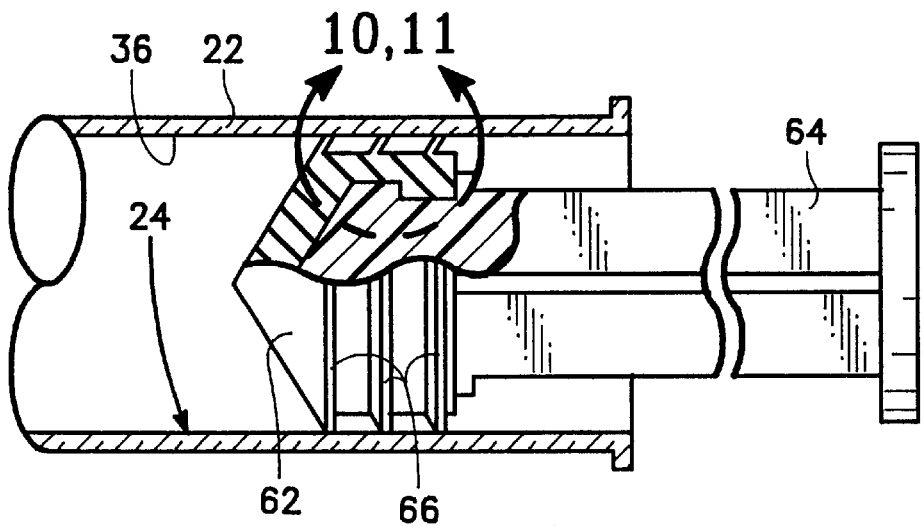
FIG. 9 is a longitudinal cross-sectional view of a syringe body stopper piston with the stopper piston and plunger mounted within an internal chamber of the syringe body showing an air discharge valve in an at-rest position.
Figure 10:
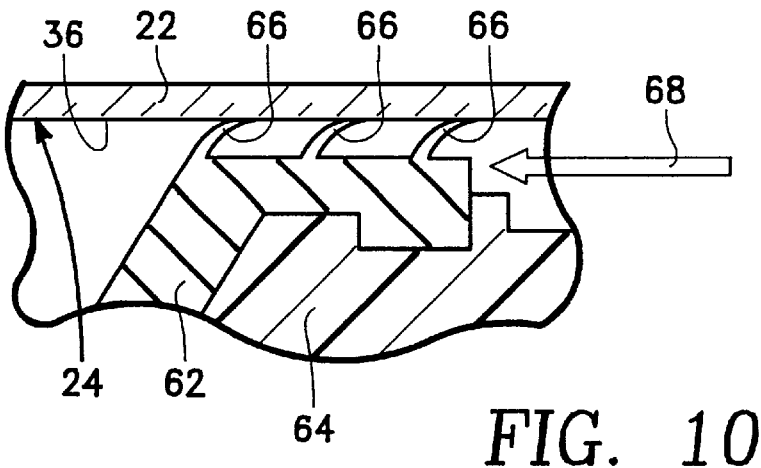
FIG. 10 is a view taken along line 10—10 of FIG. 9 depicting movement of the plunger within the internal chamber of the syringe during which time air will be discharged through the air discharge valve.
Figure 11:
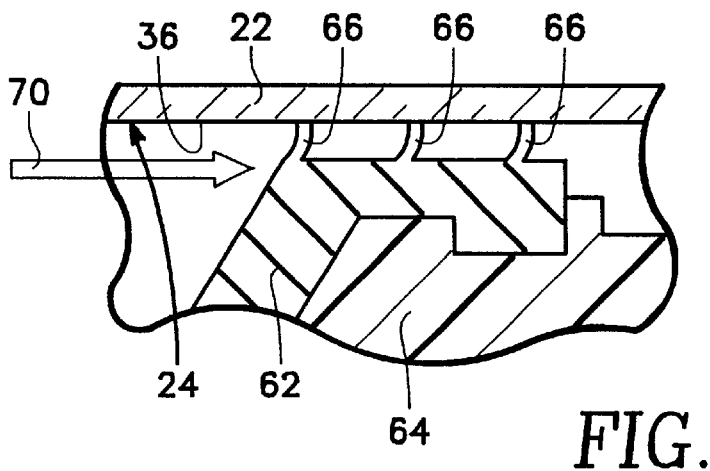
FIG. 11 is a view similar to FIG. 10 taken along line 11—11 of FIG. 9 showing movement of the plunger and stopper piston in the opposite direction which will function to create a vacuum within the front section of the internal chamber of the syringe for the purpose of drawing in a medicament or solution within this front section.

When the tube 30 is inserted within the internal chamber 58 of the female luer 60, a liquid tight fit is established between the syringe body 22 and the luer lock 42. The tip portion of the spike 44 will also protrude within the front section 34 of the internal cylindrical chamber 24. Movably mounted within the rear section 36 is a stopper piston 62. The stopper piston 62 is shown in greater detail in FIGS. 9–11. The stopper piston 62 is attached to a plunger 64. This plunger 64 is to be manually moved within the internal chamber 24 between the position shown in FIGS. 1–3 of the drawings. The sidewall of the stopper piston 62 includes a plurality of annular rings 66. These annular rings 66 are formed to form a natural laid back configuration and will normally be constructed of plastic or rubber material. The rings 66 are capable of deflecting. When force is applied to the plunger 64 tending to move the plunger 64 in the direction of arrow 68, the rings 66 will deflect and permit trapped air within the rear section 36 to escape out past the rings 66. When the plunger 64 is moved in the opposite direction as indicated by arrow 70, the rings 66 will assume a more perpendicular position relative to the wall of the rear section 36 of the internal cylindrical chamber 24, which is shown in FIG. 11. This will cause the rings 66 to create an airtight connection between the stopper piston 62 and the internal cylindrical chamber 24. The result is as plunger 64 and stopper piston 62 is moved in the direction of arrow 70, a vacuum will be created in between the stopper piston 62 and the mid-piston 38. This will result in the mid-piston 38 being moved from its forward position located directly adjacent the spike 44 to its rearwardmost position, shown in FIG. 2. Thusly, the rings 66 function as an air discharge valve opening discharging air in direction of arrow 68 and closing and creating a vacuum when piston 38 moves in the opposite direction indicated by arrow 70. At the time the plunger 64 is moved, if the luer 42 is connected to a source of liquids, such as a medicament or a solution, that liquid will be drawn into the front section 34 of the internal chamber with a selected volume of liquid 72 being shown in FIG. 2 and in FIG. 5.

There is also mounted in the rear section 36 in FIGS. 1–3 a flexible walled bag 74. The flexible walled bag 74 contains a quantity of a second liquid 76. After the desired quantity of the solution 72 has been supplied within the front section 34, the luer 42 is disconnected from the source of the solution 72 and then reconnected with the IV line or IV needle, which is not shown. At that time, forward movement of the plunger 64 in the direction of arrow 68 will cause the liquid 72 to be discharged through the outlet passage 28, through the holes 56, through discharge passage 52 and into the IV line or IV needle. When the solution 72 has been substantially emptied from the front section 34, the mid-piston 38 will be located again directly adjacent the spike 44. Further forward motion of the plunger 64 will cause the spike 44 to penetrate narrowed section 40 with the spike 44 then penetrating the flexible walled bag 74. The liquid 76 will then be capable of being conducted into the outlet passage 28, through the holes 56 and into the discharge passage 52. When the plunger 64 has been moved to its maximum forward position, the flexible walled bag 74 will be tightly compressed with substantially all of the liquid 76 having been discharged therefrom. This position is shown in FIG. 3 of the drawings.

Figure 4:
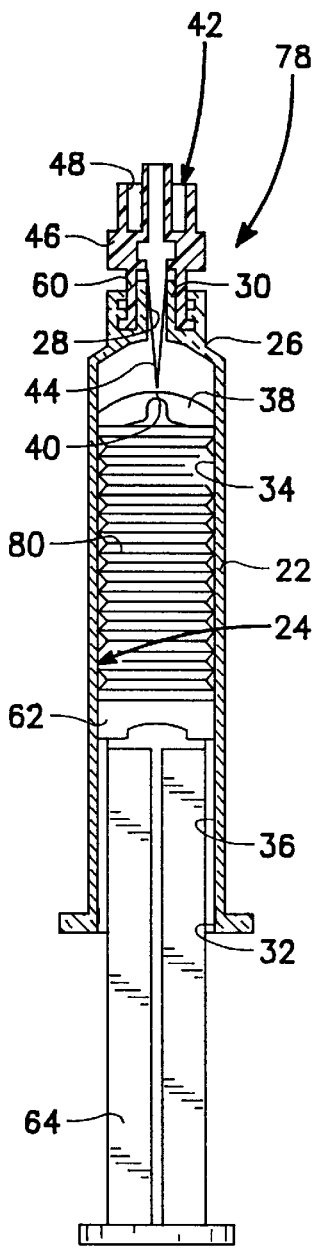
FIG. 4 is a longitudinal cross-sectional view of a second embodiment of syringe again showing the position of the syringe as it would be supplied to a hospital, doctor's office or other medical facility.
Figure 5:
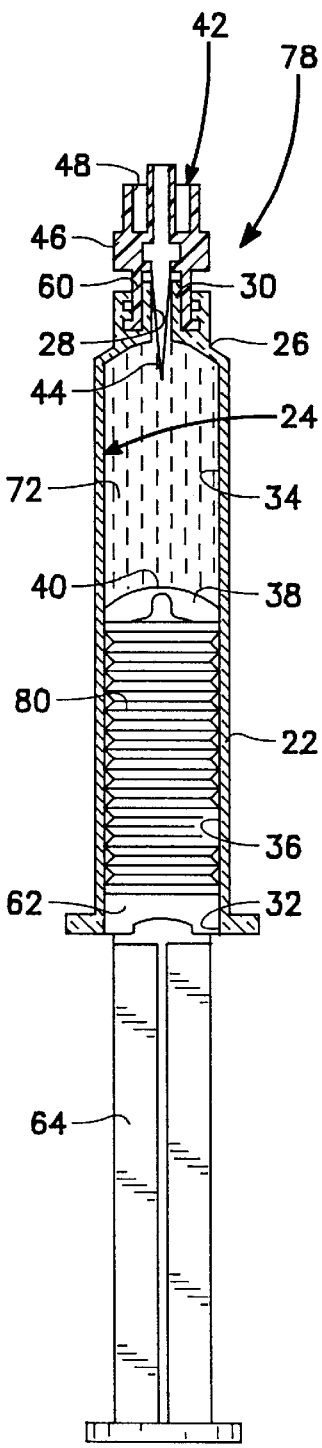
FIG. 5 is a longitudinal cross-sectional view similar to FIG. 4 but showing the syringe in the position of having added a medicament or solution within the front compartment of the syringe.
Figure 6:
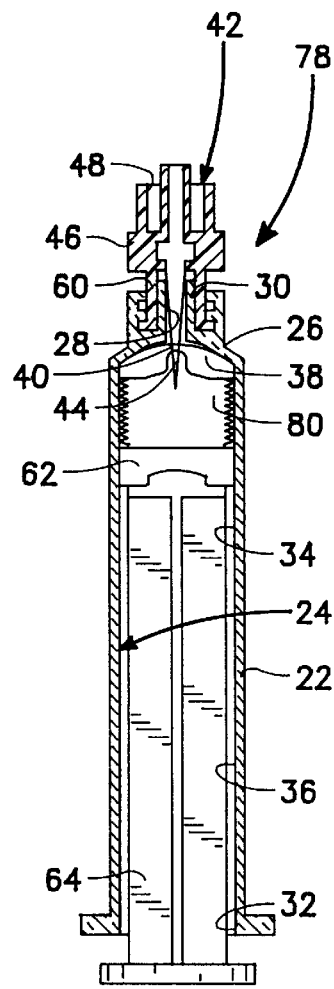
FIG. 6 is a longitudinal cross-sectional view similar to FIG. 5 but showing the syringe in the position of having discharged both liquids contained within the body of the syringe.
Figure 7:
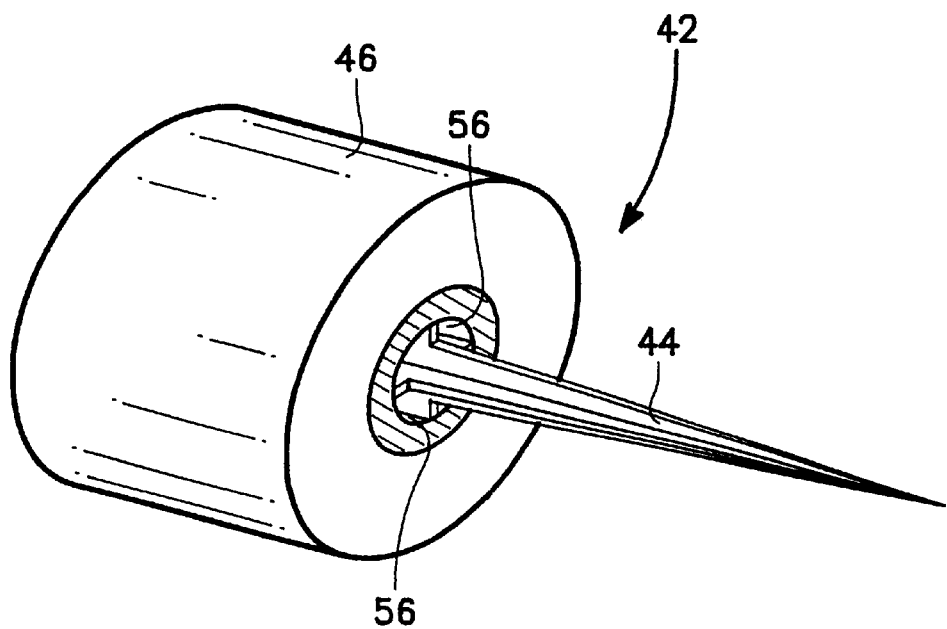
FIG. 7 is an external isometric view of the integral one-piece syringe luer that is used in conjunction with this invention.
Figure 8:
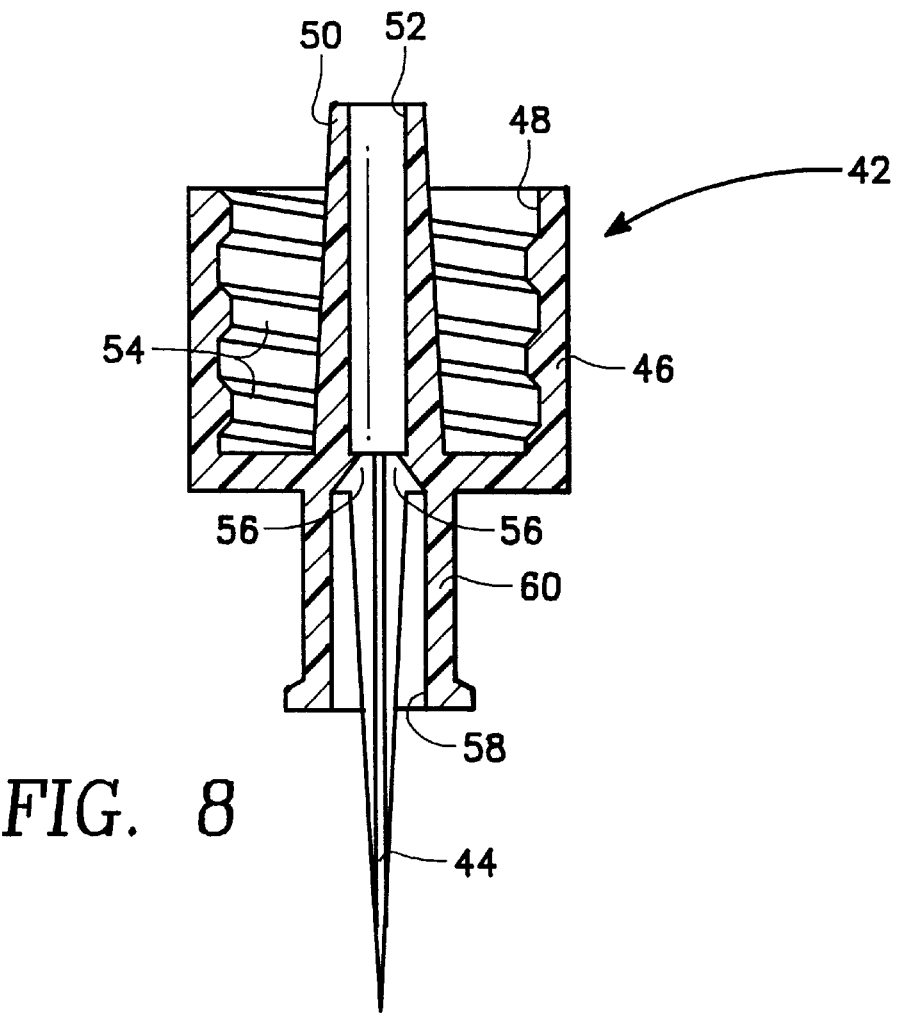
FIG. 8 is a longitudinal cross-sectional view through the integral one-piece syringe luer of FIG. 7.

Referring particularly to FIGS. 4–6 of the drawings, there is shown a similar structural arrangement to FIGS. 1–3 except of a second embodiment 78. Within FIGS. 4–6, like numerals relative to the elements described in FIGS. 1–3 have been employed. For a discussion regarding the particular parts referenced by these numerals, reference is to be had to the discussion of FIGS. 1–3. The only difference shown by the second embodiment 78 has to do with the collapsing means, instead of using the bag 74, there is utilized a bellows 80. There will be contained within the bellows 80 a second liquid similar to second liquid 76. When the plunger 64 gets very near to its most inward position as shown in FIG. 6, substantially of the solution contained within the bellows 80 will have been discharged through the discharge passage 52. It is to be understood that the second liquid 76 will follow sequentially the first liquid 72 during dispensing which will have already been discharged through the discharge passage 52. Using of both the bag 74 and bellows 80 permits manufacturing of syringe body 26 containing only one liquid 72 or no liquid and then be sterilized. The second liquid may then be added just prior to injection by the doctor or nurse by inserting the bag 74 or bellows 80 in rear section 36 and plunger 64 in rear section 36. The second liquid will be added during the manufacturing process.

Figure 12:
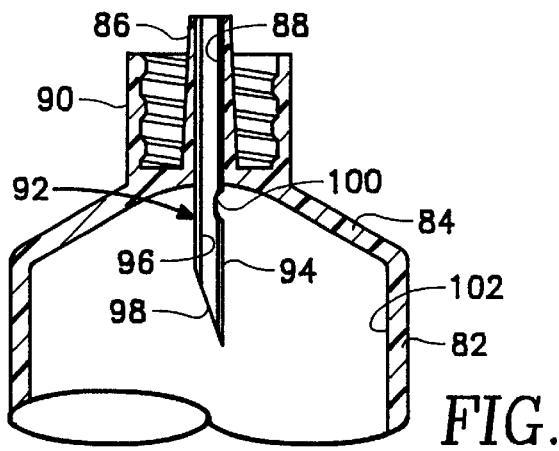
FIG. 12 is a cross-sectional view of the closed end of the syringe within which is press fittingly fixedly mounted a hollow cylindrical needle.
Figure 13:
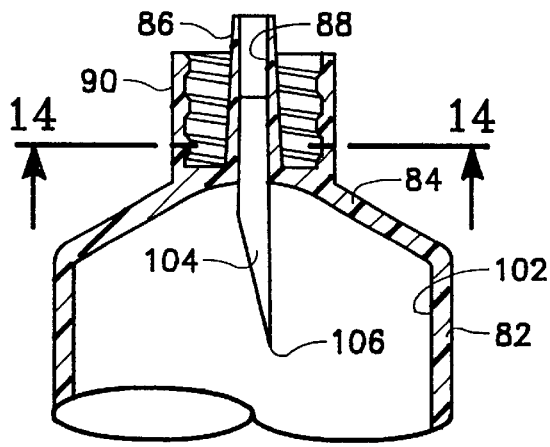
FIG. 13 is a view similar to FIG. 12 but where the piercing member has a V-shape in transverse cross-section.
Figure 14:
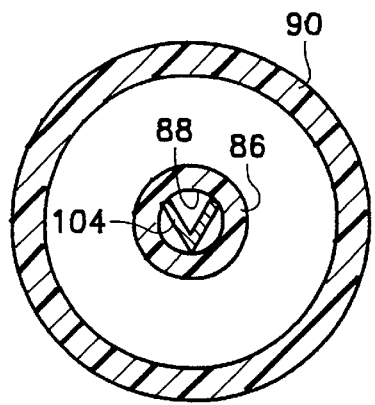
FIG. 14 is a transverse cross-sectional view taken through line 14—14 of FIG. 13.

Referring particularly to FIGS. 12–14 of the drawings, there is shown a syringe body 82 that has a substantially closed end 84. The closed end 84 has a tapered syringe liquid discharge tube 86. The tube 86 has a through passage 88. Surrounding the tube 86 is a threaded connector known as a luer lock 90.

Referring particularly to FIG. 12, there is press fittingly fixedly mounted within the through passage 88 a hollow needle 92. The hollow needle 92 has a cylindrical sidewall 94. The sidewall 94 encloses a through passage 96. The outer end of the sidewall 94 is angularly cut forming a slanted entry opening 98. Formed within the sidewall 94 and spaced from the slanted entry opening 98 is a hole 100.

It is important to note that the needle 92 is not mounted by glue or any other substance within the through passage 88 which would fixedly secure the needle 92 relative to the syringe body 82. The reason for not wanting to use an adhesive is that possibly the adhesive could contaminate the medicament or other substance that is being injected by the syringe body 82. It is for this reason that the press fitting of the needle 92 within the through passage 88 is preferred.

It is to be understood that the structure of FIG. 12 will be embodied within the syringe structures that are shown within FIGS. 1–6. When the entry opening 98 of the needle 92 penetrates either the bag 74 or the bellows 80, there will still be some of the liquid contained within the internal chamber 102. As the plunger 64 and piston 62 continues to move, the liquid that is contained within the internal chamber 102 will be permitted to be conducted through the hole 100 and be dispensed exteriorly of the through passage 96 of the needle 92 prior to the liquid that is contained within the bag 74 or the bellows 80 then being dispensed through the through passage 96.

Referring particularly to FIGS. 13 and 14, instead of using a cylindrical hollow needle 92 there is used a V-shaped piercing member 104. The outer end of the piercing member 104 is cut at an angle forming a sharpened tip 106. There is no need to use a hole, such as hole 100, because all the liquid will flow through the gap areas that are provided between the V-shaped member 104 and the through passage 88.

Figure 15:
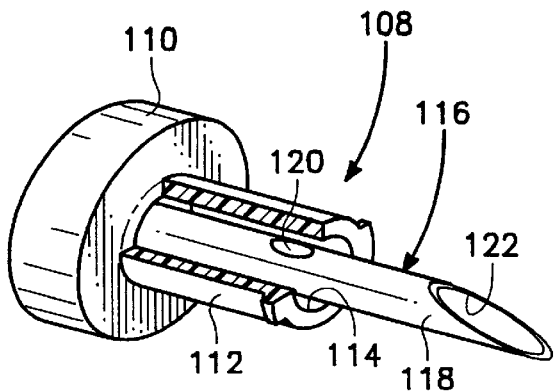
FIG. 15 is an external isometric view of a different version of one-piece syringe luer which is similar to FIG. 7.

Referring particularly to FIG. 15, there is shown a male/female luer lock 108 which is basically similar to the luer lock 42. The cylindrically shaped collar 110 of the luer lock 108 has an outwardly extending locking sleeve 112 fixedly attached thereto. The locking sleeve 112 has an internal passage 114 which is to connect with the passage, which is not shown, that extends through the collar 110. Press fittingly mounted within the passage located within the collar 110 is a hollow needle 116 which is basically identical to hollow needle 92. Hollow needle 116 has a sidewall 118 which includes a hole 120. Hole 120 is basically similar to hole 100. The outer end of the hollow needle 116 includes a slanted entry opening 122.

Figure 16:
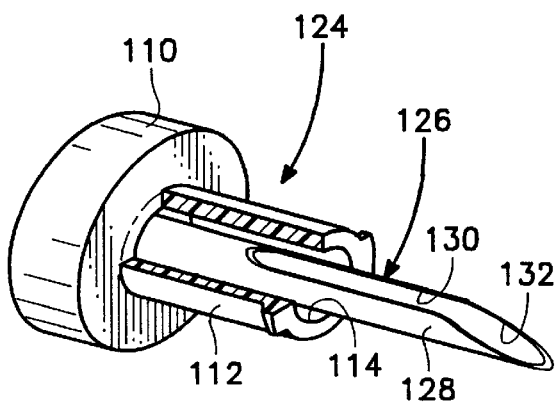
FIG. 16 is a view similar to FIG. 15 but where the piercing member has an elongated longitudinal slot instead of having a separate opening spaced from the open outer end of the hollow piercing member.

Referring particularly to FIG. 16, there is shown a male/female luer lock 124 which has a similar collar 110 and locking sleeve 112. Within the internal passage 114 of the locking sleeve 112 there is press fittingly located a different version of hollow needle 126. Instead of including of an opening of a hole 120 within the sidewall 128 of hollow needle 126, there is formed an elongated longitudinally oriented slot 130. The slot 130 extends from the entry opening 132 to within the confines of the internal passage 114. The slot 130 will also function to permit dispensing of substantially all of the liquid that is contained in the internal chamber 102 as the plunger 64, piston 64 and mid-piston 38 are moved inward toward the luer lock 124.

Figure 17:
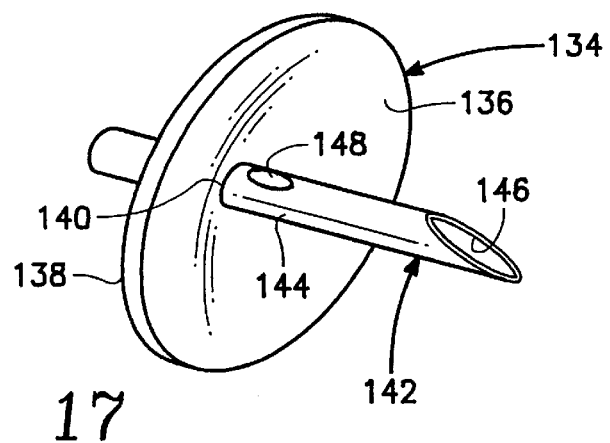
FIG. 17 is an isometric view of a further embodiment of piercing member where the piercing member is mounted on a mounting disc.

Referring particularly to FIGS. 17–20 of the drawings, there is shown a different way of manufacturing the hollow needle arrangement that has been disclosed in this invention. FIG. 17 shows a thin disc 134 which has a concave front surface 136 and a convex rear surface 138. Typically, the disc 134 will be manufactured of a plastic. Centrally formed through the disc 134 is a central hole 140. Press fittingly located within the central hole 140 is a hollow needle 142. Hollow needle 142 has a cylindrical sidewall 144 which surrounds an internal chamber access to which is provided by slanted entry opening 146. A hole 148 is provided through the sidewall 144. The hollow needle 142 extends through the disc 134 so that the needle 142 will extend from both the front surface 136 and the rear surface 138. It is preferred that the hole 148 be located directly adjacent the front surface 136.

Figures 18, 19, 20:
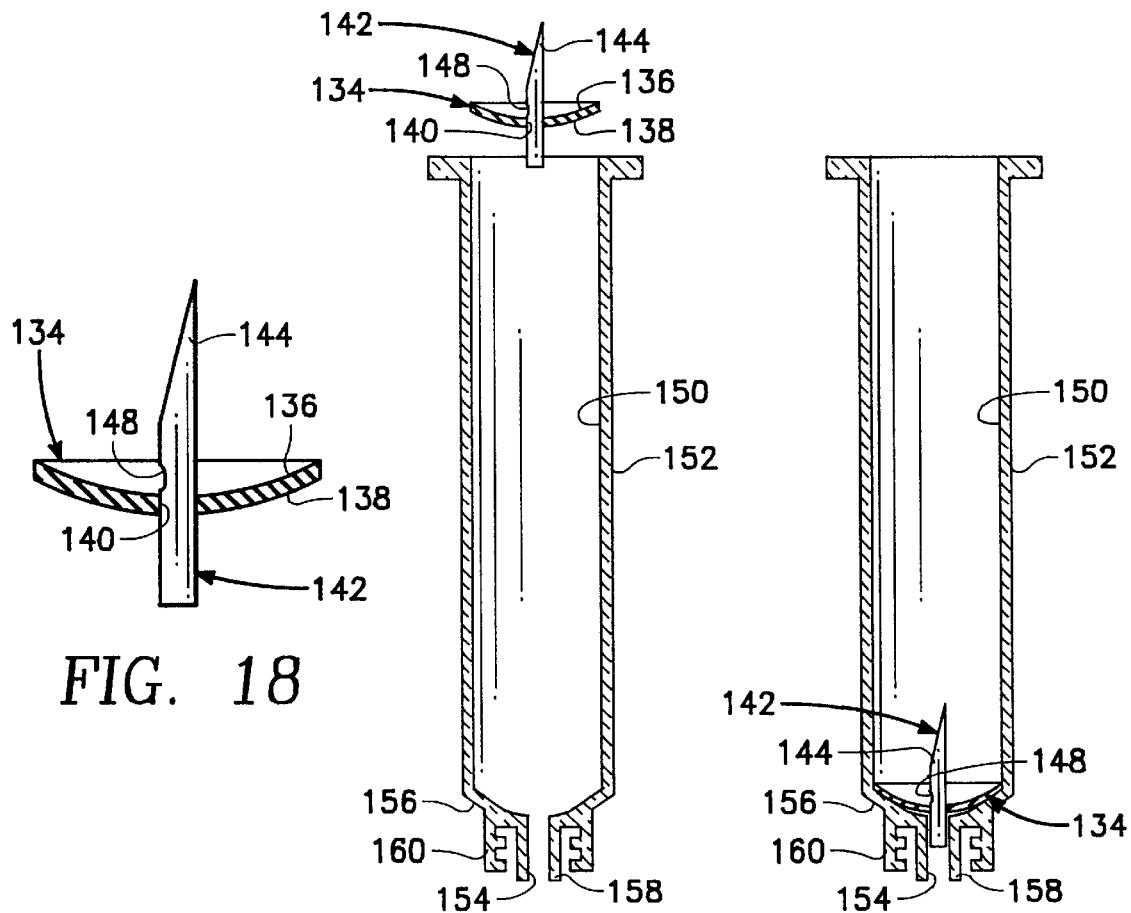
FIG. 18 is a side elevational view of the further embodiment of FIG. 17.
FIG. 19 is a longitudinal cross-sectional view through a syringe body depicting installation of the further embodiment of FIG. 17 within the internal chamber of the syringe body.
FIG. 20 is a cross-sectional view similar to FIG. 19 showing the mounting disc in its installed position within the internal chamber of the syringe body.

Referring specifically to FIGS. 19 and 20, the disc 134 is to be merely slid into internal chamber 150 of a cylindrical syringe body 152. It is to be understood that the disc 134 could be constructed other than round, such as for example, could be octagonal. In such an instance, the internal chamber 150 would have a similar octagonal configuration. The disc 134 will be slid until the inner end of the needle 142 becomes tightly press fitted within through passage 154 of the substantially closed end 156 of the syringe body 152. Through passage 154 is mounted within a tapered discharge tube 158 which has a luer lock 160 mounted there about. The needle 142 is to be used in the same manner as previously described relative to the other needles.

What is claimed is:

1. A sequential delivery syringe comprising:
   a body having an internal chamber, said body substantially closing said internal chamber at one end and being opened at an opposite end of said internal chamber;

a piercing member mounted on said one end, said piercing member extending within said internal chamber;

a mid-piston movably mounted within said internal chamber, said mid-piston dividing said internal chamber into a front section and a rear section;

a stopper piston mounted within said rear section, said stopper piston being attached to a plunger, said plunger being located within said opposite end of said internal chamber and extending exteriorly of said body;

means for collapsing mounted in said rear section, a first liquid to be contained within said means, said means being normally closed;

a second liquid to be contained within said front section, whereby upon movement of said plunger and said stopper piston toward said one end said second liquid to be discharged through said discharge passage until said mid-piston is penetrated by said piercing member which provides access into said means for collapsing and permits said first liquid to be discharged through said discharge passage;

a luer lock mounted on said one end, said luer lock having a collar which surrounds an internal annular chamber, a tapered male luer mounted to said collar and extending within said internal annular chamber, said tapered male luer being centrally mounted within said annular chamber; and said collar having a plurality of holes through which both said first liquid and said second liquid is to flow into said discharge passage.

2. The sequential delivery syringe as defined in claim 1 wherein:

said holes surround said piercing member.

3. A sequential delivery syringe comprising:

a body having an internal chamber, said body substantially closing said internal chamber at one end and being opened at an opposite end of said internal chamber;

a piercing member mounted on said one end, said piercing member extending within said internal chamber;

a mid-piston movably mounted within said internal chamber, said mid-piston dividing said internal chamber into a front section and a rear section;

a stopper piston mounted within said rear section, said stopper piston being attached to a plunger, said plunger being located within said opposite end of said internal chamber and extending exteriorly of said body;

means for collapsing mounted in said rear section, a first liquid to be contained within said means, said means being normally closed;

a second liquid to be contained within said front section, whereby upon movement of said plunger and said stopper piston toward said one end said second liquid to be discharged through said discharge passage until said mid-piston is penetrated by said piercing member which provides access into said means for collapsing and permits said first liquid to be discharged through said discharge passage; and said stopper piston including an air discharge valve, moving of said stopper piston and said plunger toward said mid-piston will cause air within said rear section to be discharged through said air discharge valve, moving of said stopper piston and said plunger away from said mid-piston will cause said air discharge valve to be closed.

4. The sequential delivery syringe as defined in claim 3 wherein:

said air discharge valve comprising a series of deflectable rings mounted on said stopper piston.

5. A sequential delivery syringe comprising:

a body having an internal chamber, said body substantially closing said internal chamber at one end and being opened at an opposite end of said internal chamber;

a piercing member mounted on said one end, said piercing member extending within said internal chamber;

a mid-piston movably mounted within said internal chamber, said mid-piston dividing said internal chamber into a front section and a rear section;

a stopper piston mounted within said rear section, said stopper piston being attached to a plunger, said plunger being located within said opposite end of said internal chamber and extending exteriorly of said body;

means for collapsing mounted in said rear section, a first liquid to be contained within said means, said means being normally closed;

a second liquid to be contained within said front section, whereby upon movement of said plunger and said stopper piston toward said one end said second liquid to be discharged through said discharge passage until said mid-piston is penetrated by said piercing member which provides access into said means for collapsing and permits said first liquid to be discharged through said discharge passage; and said piercing member being mounted on a disc, said disc having a concave front surface and a convex rear surface, said disc being placeable within said internal chamber with said convex rear surface to be located directly adjacent said one end.

* * * * *